United States Patent [19]

Baumgart et al.

[11] Patent Number: 5,211,645
[45] Date of Patent: May 18, 1993

[54] DEVICE FOR GUIDING AN INTERNAL SAW FOR LONG TUBULAR BONE OSTEOTOMY

[76] Inventors: Rainer Baumgart, Athener Platz 11, 8000 Munich 90; Augustin Betz, Am Sonnengrund 4a, 8130 Starnberg, both of Fed. Rep. of Germany

[21] Appl. No.: 656,053
[22] PCT Filed: Jul. 4, 1990
[86] PCT No.: PCT/EP90/01079
§ 371 Date: Mar. 4, 1991
§ 102(e) Date: Mar. 4, 1991
[87] PCT Pub. No.: WO91/00061
PCT Pub. Date: Jan. 10, 1991

[30] Foreign Application Priority Data

Jul. 4, 1989 [DE] Fed. Rep. of Germany ....... 3921973

[51] Int. Cl.$^5$ .................................................. A61B 17/00
[52] U.S. Cl. .......................................... 606/96; 606/86; 606/79
[58] Field of Search .................. 606/53, 79, 80, 81, 606/82, 86, 87, 96, 176

[56] References Cited

U.S. PATENT DOCUMENTS

| | | | |
|---|---|---|---|
| 3,214,869 | 11/1965 | Stryker. | |
| 3,472,229 | 10/1969 | Kuntscher | 606/176 |
| 3,867,932 | 2/1975 | Huene | 606/96 X |
| 3,892,232 | 7/1975 | Neufeld | 606/80 |
| 4,273,117 | 6/1981 | Neuhauser | 606/80 |
| 4,341,206 | 7/1982 | Perret et al. | 606/80 |
| 4,381,770 | 5/1983 | Neufeld | 606/96 X |
| 4,697,586 | 10/1987 | Gazale | 606/53 |

FOREIGN PATENT DOCUMENTS 1288241 1/1969 Fed. Rep. of Germany.
1491219 3/1971 Fed. Rep. of Germany.

OTHER PUBLICATIONS

New Instruments for the Operative Treatment of Fractures, 60Doy Moreira, KNY-Scheerer Corp., Apr. 1941.
International Search Report of application PCT/EP 90/01079 dated Nov. 16, 1990 (2 pages.).
Office Action relating to the German priority application P 39 21 973.9 dated Mar. 6, 1990 (2 pages.).

*Primary Examiner*—Robert A. Hafer
*Assistant Examiner*—Sam Rimell
*Attorney, Agent, or Firm*—John F. A. Earley; John F. A. Earley, III

[57] ABSTRACT

The device for guiding an internal saw (43) for the osteotomy of long tubular bones (50) has an elongate stem (10), a mandrel (20) which projects centrally from one end of the stem and in its peripheral surface (22), parallel with its axis, there is recessed a longitudinal groove (23) which continues in the stem (10) and through it in a longitudinal recess orientated in alignment with the longitudinal groove and it also has a spacer sleeve (30) adapted to be longitudinally displaced and fixed on the mandrel (20).

11 Claims, 3 Drawing Sheets

DEVICE FOR GUIDING AN INTERNAL SAW FOR LONG TUBULAR BONE OSTEOTOMY

The invention relates to a device for guiding an internal saw for long tubular bone osteotomy.

It is already known to cut through tubular bones from the outside, through the periosteum or from the inside, outwards from the medullary cavity, for example if the tubular bones have to be lengthened or shortened or if bone segment displacements are required.

As a rule, external osteotomy is carried out with an oscillating saw (DE-AS 1491219). Once the bone has been exposed, first the periosteum and then the substantia corticalis mentioned cortex in the following are cut through. This cutting through of the periosteum which supplies the bone's vital needs and which is rich in blood vessels, can result in vitality disorders during the recovery process.

With regard to the osteotomy outwards from the drilled out medullary cavity, in other words from the interior, the periosteal tube enclosing the tubular bone remains largely unharmed, so that vitality disorders in the region of the parting line through the bone are not anticipated.

Osteotomy from the medullary cavity is a particularly good idea if medullary nailing is involved. The access path for introduction of the medullary nail is in this case the same that is used for introduction of the internal saw, so that in the region of the osteotomy, not only the periosteal sheath but also the soft parts are intact.

In the case of osteotomy from within, a circular saw blade is used which is seated on a central arbor which is usually rotated by a compressed air drive. The arbor is guided by a guidance system which, with a slight bending action, presses the saw blade against the cortex from within (DE-AS 1288241). Since the axis of rotation of the saw blade and the axis of rotation of the guide system are inclined at an angle, there is a marked axial loading on the saw blade so that it assumes an umbrella shape. Consequently, it is no longer possible to make a clean saw cut. It has been found that the cuts made with the known guide systems are not closed but become helical and blurred.

The problem on which the invention is based therefore resides in so developing the device for guiding an internal saw for the osteotomy of long tubular bones that it is possible to achieve an exact and circular cut through the cortex from inside the medullary cavity at any desired location along a tubular bone without any substantial damage to the periosteum.

This problem is resolved by an elongate stem, by a mandrel which projects centrally from one end of the stem and in the peripheral surface of which there is recessed a longitudinal groove parallel with its axis and which continues in the stem and through the stem in a longitudinal recess which is orientated in alignment with the groove, and by a spacer sleeve adapted to be longitudinally displaced and fixed on the mandrel.

Ideally, the longitudinal groove is at least at the bottom provided with a circular cross-section, the radius of which corresponds to the longitudinal recess in the stem which is formed by an eccentric bore. So that the saw blade can saw into the cortex to its maximum depth, the depth of the longitudinal groove corresponds to the diameter of the bore or to the shaft which is guided in it.

The stem may be cylindrical in construction and may extend coaxially with the mandrel.

The saw blade with its central arbor is introduced into the drilled out medullary cavity as far as the intended osteotomy site. Then, the arbor is inserted into the longitudinal groove in the mandrel and through the bore in the stem, the saw being driven and in its position, sawing into the cortex, the final position of the device in relation to the tubular bone being determined by the previously corresponding displaced and fixed spacer sleeve. Then the device is rotated guaranteeing a perfect radial guidance of the saw blade. By means of the device according to the invention, therefore, the arbor of the internal saw which is initially displaced centrally in relation to the medullary cavity is displaced radially outwardly in the medullary cavity and into the longitudinal recess in the mandrel and the bore in the stem, after which it is rotated together with the stem and the mandrel, the axis of which now extends centrally through the medullary cavity. Since the driving shaft is completely accommodated in the longitudinal groove in the mandrel, the saw blade is over virtually its entire radial extent between its periphery and its arbor, able to penetrate the cortex.

If the device is so constructed that in an intermediate zone along its length, the mandrel has a cross-section which is reduced beyond the bottom of its longitudinal groove, then in this intermediate zone there is no guidance of the arbor so that the device can also be used in a curved medullary cavity.

A stable guidance of the arbor can be achieved if the longitudinal groove in the portion of the mandrel on the tapered side is constructed as a bore which is tangent to its peripheral surface.

The device can be inserted into the medullary canal with particular ease if the end of the mandrel opposite the stem is tapered.

Ideally, at the end of the stem which is opposite the mandrel there is an arrangement for engaging a tool which rotates the stem, for example in the form of a hexagon constructed on the peripheral surface of the stem, for engagement of an appropriate spanner, or in the form of a bore into which a radial lever can be inserted.

Furthermore, it is possible to provide passages which extend through the stem and the mandrel to carry a cooling and/or rinsing fluid and also for carrying it away, together with the saw waste. When it strikes the internal saw blade, the cooling fluid is thrown into the saw gap by centrifugal force and so flushes the sawn-out material to the discharge passage.

Examples of embodiment of the invention will be explained in greater detail hereinafter with reference to the accompanying drawings, in which.

Figure 1:
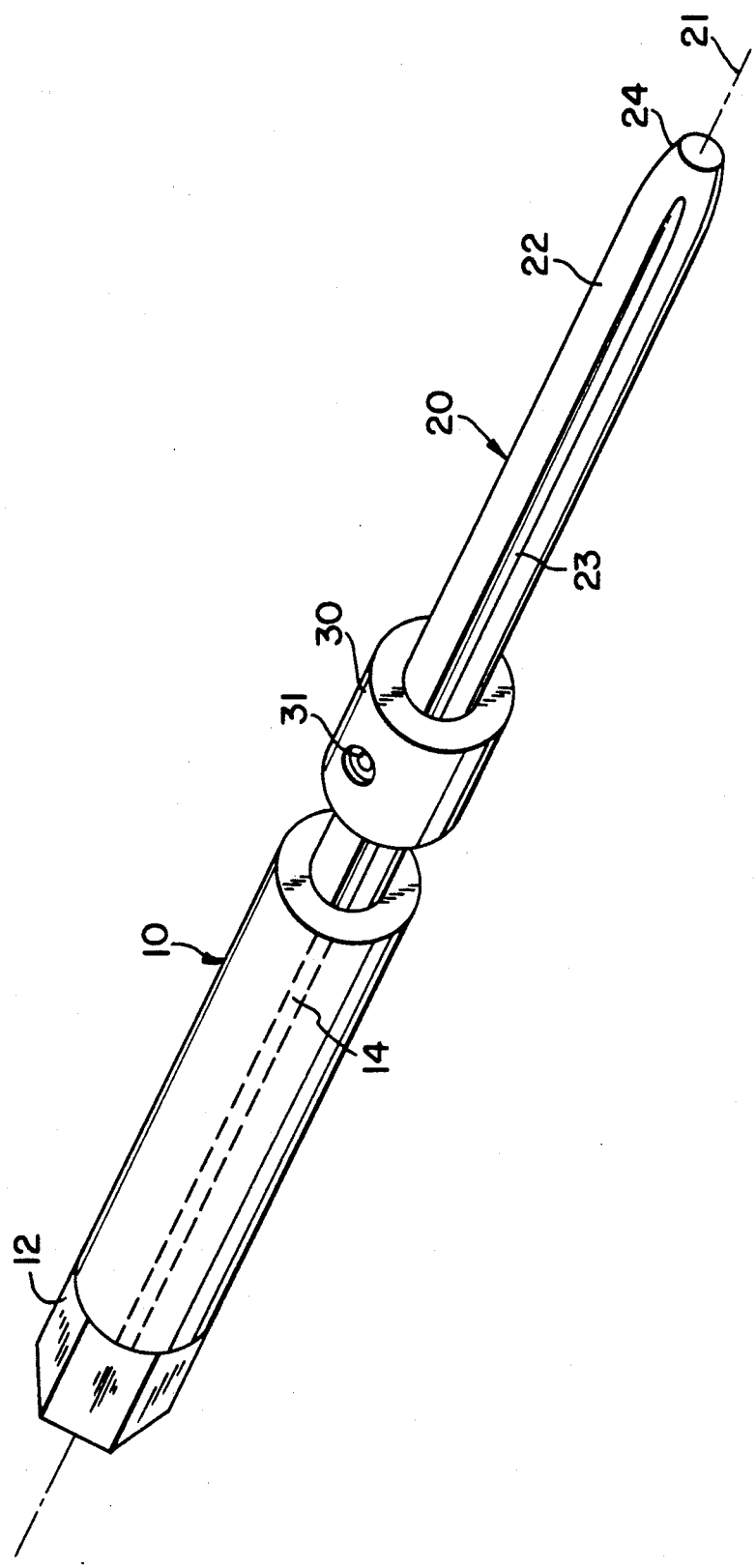
FIG. 1 is a perspective view of a first embodiment of the device.
Figure 2:
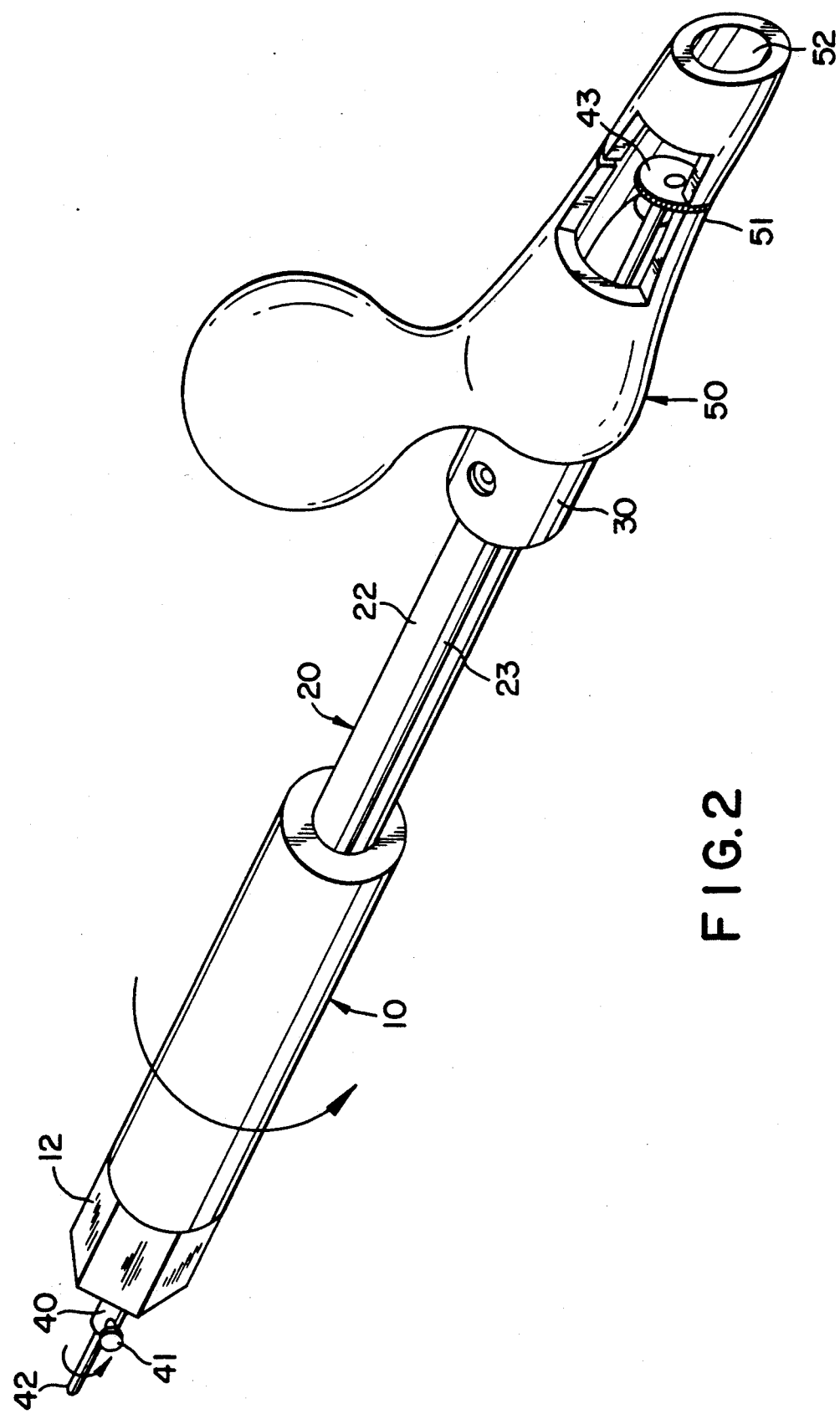
FIG. 2 shows the device according to FIG. 1 with an internal saw inserted into a tubular bone.
Figure 3:
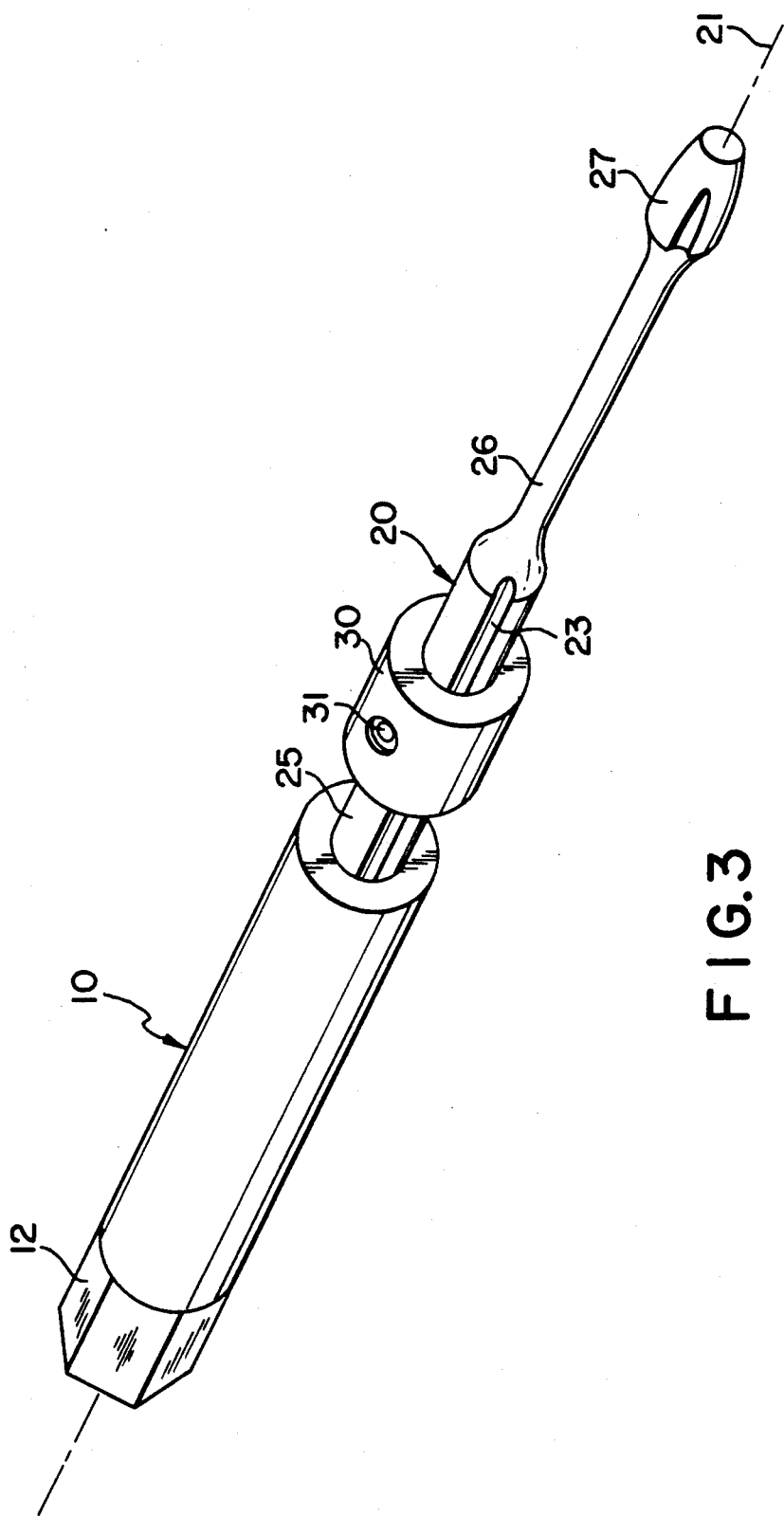
FIG. 3 is a perspective view of a second embodiment of the device.

The device shown in FIGS. 1 to 3 consists of a cylindrical stem 10 at one end of which there is a hexagon 12 while at its other end there is a coaxially projecting cylindrical mandrel 20 the diameter of which is less than that of the stem 10. Disposed for longitudinal displacement on the mandrel 20 is a spacer sleeve 30. The spacer sleeve 30 can be fixed in an adjusted axial position by means of a hexagon socket stud screw 31. The stem 10, the mandrel 20 and the spacer sleeve 30 have a common axis 21. At its free end, the mandrel 20 has a tapered portion 24.

The mandrel 20 has a peripheral surface 22 in which is recessed a longitudinal groove 23 which is parallel with the axis 21. Aligned with the longitudinal groove 23 there extends through the stem 10, parallel with the axis 21, a longitudinal recess which takes the form of a bore 14. The bore 14 and the longitudinal groove 23 are so dimensioned that they can accommodate an arbor 42 of an internal saw 43, shown in FIG. 2. For this purpose, the longitudinal groove 23 has a semi-circular bottom and side walls which extend as far as the peripheral surface 22.

In the case of the embodiment shown in FIG. 3, the mandrel 20 has at the stem end a portion 25 and at the tapered end a portion 27 along which the longitudinal groove 23 extends. Between the stem end portion 25 and the taper end portion 27 there is an intermediate portion 26 of a cross-section which is so reduced that the longitudinal groove 23 is no longer present.

If in the case of the tubular bone 50 shown in FIG. 2 the medullary cavity 52 has been drilled out in known manner, the blade seated on the arbor 42 of the internal saw 43 is introduced as far as the place where the osteotomy is to be performed. Then the arbor 42 is inserted into the longitudinal groove 23 in the mandrel 20 and through the bore 14 in the stem 10 and then out of it. Once it has been connected to a driving motor, not shown, the device, now with the arbor 42 rotating and with the axial position of the blade of the internal saw 43 unchanged, is advanced sufficiently far into the bone 50 that the spacer sleeve 30 bears against the tubular bone, this abutment position having been preset. During insertion of the device into the bone 50, the arbor 42 is already driven so that the blade of the internal saw 43 saws into the cortex at one site, making a cut 51, the depth of which, due to the proximity of the arbor 42 to the contours, corresponding to the maximum possible cutting depth of the blade of the internal saw 43. If the spacer sleeve 30 is applied at the point of entry into the tubular bone, then on the arbor 42, a clamping sleeve 40 is pushed forwards as far as the hexagon 12 on the stem 10 and fixed by means of a locking screw 41. By means of a fork wrench applied to the hexagon 12 on the stem 10, it is now possible, while the internal saw 43 is being driven, slowly to rotate the device through 360° and the blade of the internal saw 43 makes a closed annular cut 51 into the cortex of the tubular bone 50 from within the medullary cavity without making any substantial injury to the surrounding periosteum.

We claim:

1. A device for guiding an internal saw for long tubular bone osteotomy, comprising
   an elongated stem having a first end portion and a second end portion,
   a mandrel projecting centrally from the second end portion of the stem and having a free end portion, the mandrel having a peripheral surface and a longitudinal axis,
   a longitudinal groove recessed in the peripheral surface of the mandrel parallel to the longitudinal axis of the mandrel and extending to the second end portion of the stem,
   a longitudinal recess formed in the stem and aligned with the groove in the peripheral surface of the mandrel, the recess extending from the second end portion of the stem to the first end portion of the stem,
   a spacer sleeve adapted to be longitudinally displaced as desired along the mandrel, and
   fixing means for fixing the spacer sleeve on the mandrel.

2. The device of claim 1, the longitudinal recess being formed by an eccentric bore, and the longitudinal groove having a semi-circular cross-section at least in its base portion, the depth of the longitudinal groove corresponding to the diameter of the bore.

3. The device of claim 1, the stem being constructed cylindrically and coaxially with the mandrel.

4. The device of claim 1, the mandrel having an intermediate zone along its length which is coaxial with the central axis of the mandrel and has a cross-section that does not extend beyond the base portion of the longitudinal groove.

5. The device of claim 4, the longitudinal groove being formed as a bore tangent to the peripheral surface at the free end portion of the mandrel.

6. The device of claim 1, the free end portion of the mandrel being tapered.

7. The device of claim 1, further comprising engaging means disposed at the first end portion of the stem for engaging a tool to rotate the stem.

8. The device of claim 7, the engaging means being a hexagonal shaped region formed on the first end portion of the stem.

9. The device of claim 1, further comprising passages which extend through the stem and the mandrel for supplying cooling and/or rinsing fluid and for discharging the fluid with saw waste.

10. A device for guiding an internal saw for long tubular bone osteotomy, comprising
    an elongated stem having a first end portion and a second end portion,
    a mandrel projecting centrally from the second end portion of the stem and having a free end portion, the mandrel having a peripheral surface and a longitudinal axis,
    a longitudinal groove recessed in the peripheral surface of the mandrel parallel to the longitudinal axis of the mandrel and extending to the second end portion of the stem,
    a longitudinal recess formed in the stem and aligned with the groove in the peripheral surface of the mandrel, the recess extending from the second end portion of the stem to the first end portion of the stem,
    a spacer sleeve adapted to be longitudinally displaced as desired along the mandrel,
    fixing means for fixing the spacer sleeve on the mandrel,
    the longitudinal recess being formed by an eccentric bore, and the longitudinal groove having a semi-circular cross-section at least in its base portion, the depth of the longitudinal groove corresponding to the diameter of the bore,
    the stem being constructed cylindrically and coaxially with the mandrel,
    the mandrel having an intermediate zone along its length which is coaxial with the central axis of the mandrel and has a cross-section that does not extend beyond the base portion of the longitudinal groove, the longitudinal groove being formed as a bore tangent to the peripheral surface at the free end portion of the mandrel, the free end portion of the mandrel being tapered, and further comprising engaging means disposed at the first end portion of the stem for engaging a tool to rotate the stem, the engaging means being a hexagonal shaped region formed on the first end portion of the stem.

11. The device of claim 10, further comprising passages which extend through the stem and the mandrel for supplying cooling and/or rinsing fluid and for discharging the fluid with saw waste.

* * * * *